United States Patent
Gubler et al.

[11] Patent Number: 5,919,903
[45] Date of Patent: *Jul. 6, 1999

[54] LOW AFFINITY HUMAN IL-12 BETA2 RECEPTOR

[75] Inventors: Ulrich Andreas Gubler; David Howard Presky, both of Glen Ridge, N.J.

[73] Assignee: Hoffmann-La Roche Inc., Nutley, N.J.

[21] Appl. No.: 08/914,520

[22] Filed: Aug. 19, 1997

Related U.S. Application Data

[62] Division of application No. 08/685,118, Jul. 23, 1996
[60] Provisional application No. 60/018,674, May 30, 1996, and provisional application No. 60/001,701, Aug. 1, 1995.

[51] Int. Cl.$^6$ ............................................. C07K 14/705
[52] U.S. Cl. ...................... 530/350; 530/351; 930/120; 514/2; 514/8
[58] Field of Search ................................... 530/350, 351, 530/402

[56] References Cited

U.S. PATENT DOCUMENTS 5,536,657  7/1996  Chua et al. .

FOREIGN PATENT DOCUMENTS 0 638 644  2/1995  European Pat. Off. .

OTHER PUBLICATIONS

S. Grant. et al. 1990, Proc. Natl. Acad. Sci. USA 87:4645.
Gately, et al., J. Natl. Cancer Inst. 69 1245 (1982).
P. Chomczynski & N. Sacchi, Anal. Biochem. 162:156, 1987.
K. Kuribayashi et al. Nucl. Acids Res. Symposium Series 19:61, 1988.
U. Gubler & A. Chua, Essential Molecular Biology vol. II, T.A. Brown, editor pp. 39–56 TRL Press 1991.
A. Aruffo & B. Seed, Proc. Natl. Acad. Sci (USA) 94, 8573, 1987.
Hara & Miyajima 1992, EMBO 11:1875.
Grunstein & Hogness, Molecular Cloning Proc. Nat. Acad. Sci. USA 72:3961 (1975).
McPherson J., 1985, Pharmacol Methods, 14:213.
Palacios R., et al., 1985, Cell 41:727.
Giordano, T.J. et al. 1990, Gene 88:285.
vonHeijne G., 1986, Nucl. Acids Research 14:4683.
Presky, D., et al., Res. Immunol. 146 439–445 (1995).
Ellison et al., Nucl. Acid Res. 10 4071–4079.
Huck, et al., Nucl. Acid Res 14 1779–1789 (1986).
Presky, et al., PNAS 93(24), pp. 14002–14007 (1996).
Gubler, et al., FASEB J. 10(6), A1326 (1996).
Szabo et al., FASEB J. 10(6), A1310 (1996).
Gately, M.K. et al., 1991, J. Immunol. 147:874.
Kobayashi, M., et al., 1989, J. Exp. Med. 170:827.
Stern, A.S. et al., 1990, Proc. Natl. Acad Sci. USA 87:6808.
Gately, M.K., 1992, Cell Immunology 143:127.
Chan, S.H. et al., 1991, J. Exp. Med. 173:869.
Manetti, R., et al., 1993, J. Exp. Med. 177:1199.
Hsieh, C.S. et al., 1993, Science 260:547.
Chizzonite, R., et al., 1992, J. Immunol. 148:3117.
Desai, B., et al., J. Immunol, 1992, 148:3125.
Desai, B., et al., 1993, J. Immunol. 150:207A.
Chizzonite, R., et al., 1994, Cytokine 6(5):A82a.
Chua, A., et al., 1994, J. Immunology 153:128.
Stahl & Yancopoulos, 1993, Cell 74:587.
Charnow, S.M., et al., Trends in Biotechnology vol.14 52–60 (1996).
M.O. Dayhoff, et al., Methods Enzymology 91:524 (1983).
U. Gubler, et al., 1991, Proc. Natl. Acad. Sci USA 88:4143.
H.W. Lahm et al. 1985, J. Chromatog. 326:357.
S. Mizushima & S. Nagata, Nucl. Acids Res. 1990 18:5322.

*Primary Examiner*—Garnette D. Draper
*Attorney, Agent, or Firm*—George W. Johnston; Patricia S. Rocha-Tramaloni; Robert A. Silverman

[57] ABSTRACT

A recombinant human IL-12 receptor complex produced on the surface of a non-human mammalian cell and free from other human proteins, the complex comprising the beta1 receptor protein complexed with a beta2 receptor protein, which complex is capable of binding to human IL-12 with high affinity. A recombinant human IL-12 beta2 receptor protein produced on the surface of a non-human mammalian cell, free from other human proteins, in its active form. In addition, a non-human mammalian cell having expressed on its surface the recombinant human IL-12 beta2 receptor protein or the recombinant human IL-12 receptor complex, which cell proliferates in the presence of human IL-12. A non-human mammalian cell having the human IL-12 beta2 receptor protein or the complex expressed on its surface and which proliferates in response to human IL-12 is useful for determining whether a given compound inhibits biological activity of human IL-12 or is an IL-12 agonist.

2 Claims, No Drawings

LOW AFFINITY HUMAN IL-12 BETA2 RECEPTOR

This is a division of application Ser. No. 08/685,118, filed Jul. 23 1996, pending, which claims the benefit of U.S. Provisional application Ser. Nos. 60/001,701 and 60/018, 674, filed Aug. 1, 1995 and May 30, 1996, respectively, the United States.

FIELD OF INVENTION

This invention relates generally to human Interleukin-12 receptors.

BACKGROUND OF THE INVENTION

Interleukin-12 (IL-12), formerly known as cytotoxic lymphocyte maturation factor or natural killer cell stimulatory factor, is a 75-KDa heterodimeric cytokine composed of disulfide-bonded 40-KDa (p40) and 35-KDa (p35) subunits that has multiple biological activities including stimulation of the proliferation of activated T and NK cells (Gately, M. K., et al., 1991, J. Immunol., 147:874) (Kobayashi, M., et al., 1989, J. Exp. Med., 170:827), enhancement of the lytic activity of NK/LAK cells (Kobayashi, M., et al., 1989, J. Exp. Med., 170:827; Stern, A. S., et al., 1990, Proc. Natl. Acad. Sci. USA, 87:6808), enhancement of cytolytic T-cell responses (Gately, M. K., et al., 1992, Cell. Immunology, 143:127), induction of interferon gamma by resting and activated T- and NK-cells (Kobayashi, M. et al., 1989, J. Exp. Med., 170:827; Chan, S. H., et al., 1991, J. Exp. Med., 173:869), and promotion of $T_h1$-type helper cell responses (Manetti, R., et al., 1993, J. Exp. Med., 177:1199; Hsieh, C.-S., et al., 1993, Science 260:547).

The biological activity of IL-12 is mediated by the binding of the IL-12 molecules to cell surface, or plasma membrane, receptors on activated T- and NK cells; however, the contributions of the individual subunits, p35 and p40, to receptor binding and signal transduction remain unknown. Studies with labeled IL-12 have shown that this binding occurs in a specific and saturable manner. IL-12 delivers a signal to target cells through a receptor that was initially characterized on phytohaemagglutinin (PHA)-activated CD4+ and CD8+ T-cells and on IL-2 activated CD56+ NK-cells (Chizzonite, R., et al., 1992, J. Immunol., 148:3117; Desai, B., et al., 1992, J. Immunol., 148:3125).

A survey of over 20 human cell lines belonging to the T-, B-, NK- and myelomonocytic lineages only identified a single CD4+, IL-2 dependent human T-cell line (Kit 225/K6) that constitutively expresses the IL-12 receptor and responds to IL-12 (Desai, B., et al., 1992, J. Immunol., 148:3125; Desai, B., et al., 1993, J. Immunol. 150:207A). Freshly prepared PHA-activated peripheral blood mononuclear cells (PBMC) and the Kit 225/K6 cell line thus represent two convenient cell sources to study the biochemistry of the functional IL-12 receptor; there may be others.

Equilibrium binding experiments with $^{125}$I-labeled IL-12 identified three sites with binding affinities for human IL-12 of 5–20 pM, 50–200 pM, and 2–6 nM on IL-12 responsive T-cells (Chizzonite, R., et al., 1994, Cytokine 6(5):A82a).

A cDNA encoding a low affinity IL-12 receptor was previously cloned (Chua, A., et al, 1994, J. Immunology 153:128; U.S. patent application Ser. No. 08/248,532, filed May 31, 1994 (incorporated herein by reference)). Based on a previously suggested nomenclature (Stahl and Yancopoulos, 1993, Cell 74:587), we now call the initially isolated human IL-12 receptor chain the beta1 chain. However, because (i) this isolated human IL-12 beta1 receptor chain binds human IL-12 with low affinity, and (ii) IL-12 responsive T-cells have a high affinity binding site for human IL-12, another human IL-12 receptor chain must exist.

SUMMARY OF THE INVENTION

We have found that the IL-12 receptor comprises a complex of the beta1 receptor protein with a beta2 receptor protein, which complex is capable of binding to human IL-12 with high affinity. We have isolated the DNA encoding the human IL-12 beta2 receptor protein and produced a recombinant human IL-12 beta2 receptor protein on the surface of a non-human mammalian cell, free from other human proteins, in its active form. In addition, we produced a recombinant human IL-12 receptor complex on the surface of a non-human mammalian cell, free from other human proteins, having a high binding affinity for human IL-12. In addition, we produced a non-human mammalian cell having expressed on its surface the recombinant human IL-12 beta2 receptor protein, which cell proliferates in the presence of human IL-12. In addition, we produced a non-human mammalian cell having expressed on its surface the recombinant human IL-12 receptor complex, which cell proliferates in the presence of human IL-12.

In accordance with this invention, a non-human mammalian cell having the human IL-12 beta2 receptor protein or the complex expressed on its surface and which proliferates in response to human IL-12 is useful for determining IL-12 bioactivity. For example, such cells are useful for determining whether a given compound inhibits biological activity of human IL-12 or is an IL-12 agonist.

In addition, through the ability to express the human IL-12 beta2 receptor protein on a non-human mammalian cell surface, we can also express fragments of the human IL-12 beta2 receptor protein, and can determine whether these fragments, when complexed with the beta1 subunit, or an active fragment thereof, have the same properties and high binding affinity for IL-12 as the intact complex.

We can use the isolated DNA encoding the human IL-12 beta2 receptor protein to make a purified, recombinant protein which is soluble, and which binds to IL-12 with the same affinity as human IL-12 beta2 receptor protein. We can also use the isolated DNA encoding the human IL-12 beta2 receptor protein to make a purified, recombinant protein which is soluble, and which binds to IL-12 with the same affinity as the recombinant human IL-12 receptor complex of the beta1 receptor protein with the beta2 receptor protein [See, for example, Charnow, S. M. et al., Trends in Biotechnology, Vol. 14, 52–60 (1996)].

Such purified, recombinant proteins, which bind to human IL-12, are useful for preventing or treating pathological conditions caused by excess or inappropriate activity of cells possessing IL-12 receptors, by inhibiting binding of IL-12 to such cells. Pathological conditions caused by excess activity of cells possessing IL-12 receptors include autoimmune dysfunctions, such as without limitation rheumatoid arthritis, inflammatory bowel disease, and multiple sclerosis.

A purified, recombinant protein which is soluble, and which binds to IL-12 with the same affinity as human IL-12 beta2 receptor protein is the fusion of a soluble fragment of human IL-12 beta2 receptor protein and a human Ig heavy chain (such as IgG, IgM or IgE, preferably IgG) having all domains except the first domain of the constant region. This recombinant protein is encoded by a chimeric polynucleotide which has 2 DNA subsequences fused in frame. The first DNA subsequence, at the 5' end of the chimeric polynucleotide, is an isolated DNA sequence encoding a soluble fragment of human IL-12 beta2 receptor protein. The second DNA subsequence, located at the 3' end of the chimeric polynucleotide, is an isolated DNA sequence encoding all domains of a human heavy chain Ig (preferably IgG) except the first domain of the constant region. The desired recombinant protein can be generated by transfection of the chimeric polynucleotide into a non-human mammalian cell, such as a chinese hamster ovary (CHO) cell. The expressed recombinant protein can be purified, for example, by protein G affinity chromatography.

A purified, recombinant protein which is soluble, and which binds to IL-12 with the same affinity as the recombinant human IL-12 receptor complex of the beta1 receptor with the beta2 receptor is encoded by two chimeric polynucleotides which each have two DNA subsequences fused in frame. The first DNA subsequence of the first chimeric polynucleotide, located at the 5' end, is an isolated DNA sequence encoding a soluble fragment of human IL-12 beta2 receptor protein. The second DNA subsequence of the first chimeric polynucleotide, located at the 3' end, is an isolated DNA sequence encoding all domains of a human Ig heavy chain (for example, IgG, IgM, IgE, preferably IgG) except the first domain of the constant region. The first DNA subsequence of the second chimeric polynucleotide, located at the 5' end, is an isolated DNA sequence encoding a soluble fragment of human IL-12 beta1 receptor protein. The second DNA subsequence of the second chimeric polynucleotide, located at the 3' end, is an isolated DNA sequence encoding all domains of a human Ig heavy chain (for example, IgG, IgM, IgE, preferably IgG) except the first domain of the constant region. The desired recombinant protein may be generated by cotransfection of the two chimeric polynucleotides into a non human mammalian cell, such as a CHO cell. The expressed protein can be purified, for example, by any method that enables differentiation of homodimeric proteins from heterodimeric proteins, such as, for example, column chromatography.

In addition, monoclonal or polyclonal antibodies directed against the human IL-12 beta2 receptor protein, or fragments thereof, or the complex, may also be produced by known methods [See, for example, Current Protocols in Immunology, edt. by Coligan, J. E. et al., J. Wiley & Sons (1992)] and used to prevent or treat pathological conditions caused by excess activity of cells possessing IL-12 receptors by inhibiting binding of IL-12 to such cells.

DETAILED DESCRIPTION OF THE INVENTION

We have found that the human IL-12 receptor comprises a complex of the beta1 receptor protein with the beta2 receptor protein, which complex is capable of binding to human IL-12 with high affinity. We have isolated the DNA encoding the human IL-12 beta2 receptor protein and produced a recombinant human IL-12 beta2 receptor protein on the surface of a non-human mammalian cell, free from other human proteins, in its active form. In addition, we produced a recombinant human IL-12 receptor complex on the surface of a non-human mammalian cell, free from other human proteins, having a high binding affinity for human IL-12. In addition, we produced a non-human mammalian cell having expressed on its surface the recombinant human IL-12 beta2 receptor protein, which cell proliferates in the presence of human IL-12. In addition, we produced a non-human mammalian cell having expressed on its surface the recombinant human IL-12 receptor complex, which cell proliferates in the presence of human IL-12.

The following terms shall have the following definitions set forth below:

Human IL-12 beta2 receptor protein refers to (1) the protein of SEQ ID NO:2, or (2) any protein or polypeptide having an amino acid sequence which is substantially homologous to the amino acid sequence SEQ ID NO:2 and which has the following properties:

1) The protein or polypeptide has low binding affinity for human IL-12, and
2) The protein or polypeptide, when complexed with human beta1 receptor protein forms a complex having high binding affinity for human IL-12.

Human IL-12 beta1 receptor protein refers to (1) the protein of SEQ ID NO:4, or (2) any protein or polypeptide having an amino acid sequence which is substantially homologous to the amino acid sequence SEQ ID NO:4 and which has the following properties:

1) The protein or polypeptide binds to has low binding affinity for human IL-12, and
2) The protein or polypeptide, when complexed with human beta2 receptor protein forms a complex having high binding affinity for human IL-12.

As used herein, the terms human IL-12 beta2 receptor protein and human IL-12 beta1 receptor protein includes proteins modified deliberately, as for example, by site directed mutagenesis or accidentally through mutations.

Substantially homologous, which can refer both to nucleic acid and amino acid sequences, means that a particular subject sequence, for example, a mutant sequence, varies from the reference sequence by one or more substitutions, deletions, or additions, the net effect of which do not result in an adverse functional dissimilarity between the reference and subject sequences. For purposes of the present invention, sequences having greater than 95% homology, equivalent biological properties, and equivalent expression characteristics are considered substantially homologous. For purposes of determining homology, truncation of the mature sequence should be disregarded. Sequences having lesser degrees of homology, comparable bioactivity, and equivalent expression characterisitics are considered substantial equivalents. Generally, homologous DNA sequences can be identified b y cross-hybridization under high stringency hybridization conditions.

Fragment of the human IL-12 beta2 receptor protein means any protein or polypeptide having the amino acid sequence of a portion or fragment of human IL-12 beta2 receptor protein, and which (a) has low binding affinity for human IL-12, and (2) when complexed with a human IL-12 beta1 receptor protein, forms a complex having high binding affinity for human IL-12.

Fragment of the human IL-12 beta1 receptor protein means any protein or polypeptide having the amino acid sequence of a portion or fragment of human IL-12 beta1 receptor protein, and which when complexed with a human IL-12 beta2 receptor protein, forms a complex having high binding affinity for human IL-12.

Expression vector is a genetic element capable of replication under its own control, such as a plasmid, phage or cosmid, to which another DNA segment may be attached so as to bring about the replication of the attached segment. It comprises a transcriptional unit comprising an assembly of (1) a genetic element or elements having a regulatory role in gene expression, for example, promoters and enhancers, (2) a structural or coding sequence which is transcribed into mRNA and translated into protein, and (3) appropriate transcription initiation and termination sequences.

Clone is a group of identical DNA molecules derived from one original length of DNA sequence and produced by a bacterium or virus using genetic engineering techniques, often involving plasmids.

Soluble fragment refers to a fragment of a human IL-12 receptor protein having an amino acid sequence corresponding to all or part of the extracellular region of the protein and which retains the IL-12 binding activity of the intact IL-12 receptor protein. For example, a soluble fragment of a human IL-12 beta2 receptor protein is a fragment of a human IL-12 beta2 receptor protein having an amino acid sequence corresponding to all or part of the extracellular region of a human IL-12 beta2 receptor protein.

Expression of Human IL-12 Receptor Protein Having High Binding Affinity to Human IL-12

The cDNA of cells where the human IL-12 receptor is known to be found is incorporated by conventional methods into a bacterial host to establish a cDNA library. PHA-activated PBMC and cells from the Kit 225/K6 cell line are examples of cell sources for the cDNA. RNA from the cells is extracted, characterized, and transcribed into single stranded cDNA by conventional methods. The single stranded cDNA is converted into double stranded cDNA by conventional methods. The double stranded cDNA is incorporated by conventional techniques into an expression vector, such as pEF-BOS. The plasmid DNA from the expression vector is then incorporated into a bacterial host by conventional methods to form a library of recombinants.

The cDNA library is screened by conventional expression screening methods, as described by Hara and Mijayima, 1992, EMBO, 11:1875, for cDNA's which when expressed with cDNA's for the human IL-12 beta1 receptor protein, give rise to a high affinity human IL-12 receptor. A small number of clones from the library are grown in pools. DNA is extracted by conventional methods from the pools of clones. The DNA extracted from a pool of clones is then transfected by conventional methods, along with a small amount of DNA from a plasmid containing the cDNA encoding the human IL-12 beta1 receptor protein, into non-human host cells. The non-human host cells are preferably mammalian, such as a COS cell. Labeled recombinant human IL-12 is then added to the non-human host cells previously transfected as described above and the binding signal of the pool is determined. This process is repeated for each pool. The pools showing a positive binding signal for IL-12 may then be subsequently broken down into smaller pools and reassayed in the above manner until a single clone is selected which shows a positive binding signal.

The plasmid DNA from the selected clone is sequenced on both strands using conventional methods, such as an ABI automated DNA sequencer in conjunction with a thermostable DNA polymerase and dye-labeled dideoxynucleotides as terminators. Amino acid sequence alignments may be run as described by M. O. Dayhoff et al., Methods Enzymology 91:524 (1983) with the mutation data matrix, a break penalty of 6 and 100 random runs.

The DNA from the selected clone is then co-transfected by conventional methods with DNA from a plasmid containing the cDNA encoding the human IL-12 beta1 receptor protein into a non-human host cell, preferably a non-human mammalian cell such as a COS cell or a Ba/F3 cell.

Alternatively, by conventional recombinant methods, a plasmid may be engineered which contains transcription units (promoter, cDNA, and polyA regions) for both human IL-12 beta1 receptor protein and human IL-12 beta2 receptor protein. Plasmid DNA is transfected by conventional methods into a non-human host cell, preferably a non-human mammalian cell such as a COS cell or a Ba/F3 cell.

In accordance with the invention, a complex comprising human IL-12 beta2 receptor protein, or a fragment thereof, complexed with human IL-12 beta1 receptor protein, or a fragment thereof, may be expressed on the cell surface of the non-human host cell. When expressed on the cell surface of the non-human host cell, the complex has a high binding affinity for human IL-12, whereas the human IL-12 beta1 receptor protein and the human IL-12 beta2 receptor protein alone each have a low binding affinity for human IL-12.

In accordance with this invention, we can also express on the surface of a non-human host cell human IL-12 beta2 receptor protein.

In accordance with this invention, not only can the human IL-12 beta2 receptor protein be obtained, we can also obtain fragments of human IL-12 beta2 receptor protein which (1) has low binding affinity for human IL-12 and (2) which when complexed with a human IL-12 beta1 receptor protein forms a complex having high binding affinity. The fragments of human IL-12 beta2 receptor protein may be obtained by conventional means, such as (i) proteolytic degradation of the human IL-12 beta2 receptor protein, (ii) chemical synthesis by methods routine in the art, or (iii) standard recombinant methods.

For purposes of the present invention, a human IL-12 receptor protein which has a high binding affinity for human IL-12 is a protein which binds to human IL-12 with a binding affinity of from about 5 to about 100 pM. For purposes of the present invention, a human IL-12 receptor protein which has a low binding affinity for human IL-12 is a protein which binds to human IL-12 with a binding affinity of from about 1 to about 10 nM. The binding affinity of a protein for human IL-12 can be determined by conventional means, such as desribed in R. Chizzonite et al., 1992, J. Immunol., 148:3117 and as set forth in Example 5.

Fragments of human IL-12 beta2 receptor protein can also be measured for binding affinity for human IL-12 by conventional means, such as desribed in R. Chizzonite et al., 1992, J. Immunol., 148:3117 and as set forth in Example 5. The fragments of human IL-12 beta2 receptor protein may be measured for binding affinity for human IL-12 either alone or complexed with human IL-12 beta1 receptor protein, or a fragment of human IL-12 beta1 receptor protein which when complexed with a human IL-12 beta2 receptor protein forms a complex having high binding affinity.

In accordance with this invention, we can isolate DNA which encodes a complex capable of binding to human IL-12 with high affinity, the complex comprising human IL-12 beta2 receptor protein, or a fragment thereof, and human IL-12 beta1 receptor protein, or a fragment thereof.

In accordance with this invention, we can also isolate DNA which encodes human IL-12 beta2 receptor protein, or a fragment thereof, which fragment (1) has low binding affinity for human IL-12 and (2) when complexed with human IL-12 beta1 receptor protein, forms a complex having high binding affinity for human IL-12.

An isolated DNA sequence refers to a DNA polymer, in the form of a separate fragment or as a component of a larger DNA construct, which has been derived from DNA isolated at least once in substantially pure form, that is, free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used as a source of coding sequences. Sequences of non-translated DNA may be present 5' or 3' from the open reading frame, where the same do not interfere with manipulation or expression of the coding regions.

In accordance with this invention, we can also make, by known methods, a purified, recombinant protein which is the fusion of a soluble fragment of human IL-12 beta2 receptor protein and a human Ig heavy chain (preferably IgG) containing all domains except the first domain of the constant region. This recombinant protein, which is homodimeric, is encoded by a chimeric polynucleotide which has 2 DNA subsequences fused in frame. The first DNA subsequence, at the 5' end of the chimeric polynucleotide, is an isolated DNA sequence encoding a soluble fragment of human IL-12 beta2 receptor protein. The second DNA subsequence, located at the 3' end of the chimeric polynucleotide, is an isolated DNA sequence encoding all domains of a human Ig heavy chain (preferably IgG) except the first domain of the constant region.

In addition, we can make, by known methods, a purified, recombinant protein comprising two different polypeptide chains (a heterodimeric protein). The two different polypeptide chains are each encoded by a different chimeric polynucleotide which has two DNA subsequences fused in frame. The first DNA subsequence of the first chimeric polynucleotide, located at its 5' end, is an isolated DNA sequence encoding a soluble fragment of human IL-12 beta2 receptor protein. The second DNA subsequence of the first chimeric polynucleotide, located at its 3' end, is an isolated DNA sequence encoding all domains of a human Ig heavy chain (preferably IgG) except the first domain of the constant region. The first DNA subsequence of the second chimeric polynucleotide, located at its 5' end, is an isolated DNA sequence encoding a soluble fragment of human IL-12 beta1 receptor protein. The second DNA subsequence of the second chimeric polynucleotide, located at its 3' end, is an isolated DNA sequence encoding all domains of a human Ig heavy chain (preferably IgG) except the first domain of the constant region.

The starting materials for the purified, recombinant proteins of the invention may be obtained by methods known in the art. In particular, on the basis of the DNA sequence coding for human IL-12 beta2 receptor protein described in SEQ ID NO:1 and of the already known DNA sequences for certain receptors, those partial DNA sequences which code for a soluble fragment of human IL-12 beta2 receptor protein can be determined and engineered from the DNA sequence coding for human IL-12 beta2 receptor protein described in SEQ ID NO:1 using known methods, see Sambrook et al., "Molecular Cloning", 2nd ed., Cold Spring Harbor Laboratory Press (1989). Similarly, on the basis of the DNA sequence coding for human IL-12 beta1 receptor protein described in SEQ ID NO:3 and of the already known DNA sequences for certain receptors, those partial DNA sequences which code for a soluble fragment of human IL-12 beta1 receptor protein can be determined and engineered from the DNA sequence coding for human IL-12 beta1 receptor protein described in SEQ ID NO:3 using known methods, see Sambrook et al., "Molecular Cloning", 2nd ed., Cold Spring Harbor Laboratory Press (1989). Sources for isolated DNA sequences coding for constant domains of human immunoglobulins are known in the art and disclosed, for example, by Ellison et al., Nucl. Acid Res. 10, 4071–4079 (1982) for $IgG_1$ or Huck et al., Nucl. Acid Res. 14, 1779–1789 (1986) for $IgG_3$.

The isolated DNA sequence encoding the soluble fragment of human IL-12 beta2 receptor protein may be fused in frame, by known methods [Sambrook et al., "Molecular Cloning", 2nd ed., Cold Spring Harbor Laboratory Press (1989)], to the isolated DNA sequence encoding all domains of a human Ig heavy chain (preferably IgG) except the first domain of the constant region. The resulting chimeric polynucleotide has located at its 5' end the isolated DNA sequence encoding the soluble fragment of human IL-12 beta2 receptor protein and at its 3' end the isolated DNA sequence encoding all domains of the human Ig heavy chain except the first domain of the constant region.

Similarly, the isolated DNA sequence encoding the soluble fragment of human IL-12 beta1 receptor protein may be fused in frame, by known methods [Sambrook et al., "Molecular Cloning", 2nd ed., Cold Spring Harbor Laboratory Press (1989)], to the isolated DNA sequence encoding all domains of a human Ig heavy chain (preferably IgG) except the first domain of the constant region. The resulting chimeric polynucleotide has located at its 5' end the isolated DNA sequence encoding the soluble fragment of human IL-12 beta1 receptor protein and at its 3' end the isolated DNA sequence encoding all domains of a human Ig heavy chain except the first domain of the constant region.

The chimeric polynucleotides can then be integrated using known methods [Sambrook et al., "Molecular Cloning", 2nd ed., Cold Spring Harbor Laboratory Press (1989)] into suitable expression vectors for expression in a non-human mammalian cell, such as a CHO cell. In order to make the homodimeric protein of the invention, the chimeric polynucleotide having located at its 5' end the isolated DNA sequence encoding the soluble fragment of human IL-12 beta2 receptor protein is integrated into a suitable expression vector. In order to make the heterodimeric protein of the invention, the chimeric polynucleotide having located at its 5' end the isolated DNA sequence encoding the soluble fragment of human IL-12 beta2 receptor protein and the chimeric polynucleotide having located at its 5' end the isolated DNA sequence encoding the soluble fragment of human IL-12 beta1 receptor protein are integrated into a single suitable expression vector, or two separate suitable expression vectors.

Preferably, the chimeric polynucleotide(s) is/are co-transfected together with a selectable marker, for example neomycin, hygromycin, dihydrofolate reductase (dhfr) or hypoxanthin guanine phosphoribosyl transferase (hgpt) using methods which are known in the art. The DNA sequence stably incorporated in the chromosome can subsequently be amplified. A suitable selection marker for this is, for example, dhfr. Mammalian cells, for example, CHO cells, which contain no intact dhfr gene, are thereby incubated with increasing amounts of methotrexate after transfection has been performed. In this manner, cell lines which contain a higher number of the desired DNA sequence than the unamplified cells can be obtained.

The baculovirus expression system can also be used for the expression of recombinant proteins in insect cells. Post-translational modifications performed by insect cells are very similar to those occurring in mammalian cells. For the production of a recombinant baculovirus which expresses the desired protein a transfer vector is used. A transfer vector is a plasmid which contains the chimeric polynucleotide(s) under the control of a strong promoter, for example, that of the polyhedron gene, surrounded on both sides by viral sequences. The transfer vector is then transfected into the insect cells together with the DNA sequence of the wild type baculovirus. The recombinant viruses which result in the cells by homologous recombination can then be identified and isolated according to known methods. When using the baculovirus expression system, DNA sequences encoding the immunoglobulin part have to be in the form of cDNA.

The expressed recombinant protein may be purified, for example, by known methods. For example, protein G affinity chromatography may be used to purify the homodimeric protein of the invention. Column chromatography, or any other method that enables differentiation between homodimeric proteins and heterodimeric proteins, may be used to purify the heterodimeric protein of the invention.

Such purified, recombinant proteins are useful for preventing or treating pathological conditions caused by excess or inappropriate activity of cells possessing IL-12 receptors by inhibiting binding of IL-12 to such cells.

"Purified", as used to define the purity of a recombinant protein encoded by the combined DNA sequences described above, or protein compositions thereof, means that the protein or protein composition is substantially free of other proteins of natural or endogenous origin and contains less than about 1% by mass of protein contaminants residual of production processes. Such compositions, however, can contain other proteins added as stabilizers, carders, excipients or co-therapeutics. A protein is purified if it is detectable, for example, as a single protein band in a polyacrylamide gel by silver staining.

Purified recombinant proteins as described above (as well as antibodies to the human IL-12 beta2 receptor proteins and fragments thereof, and antibodies to the complex of this invention) can be administered in clinical treatment of autoimmune dysfunctions, such as without limitation rheumatoid arthritis, inflammatory bowel disease and multiple sclerosis.

The purified recombinant proteins described above (as well as antibodies to the human IL-12 beta2 receptor proteins and fragments thereof, and antibodies to the complex of this invention) can be used in combination with other cytokine antagonists such as antibodies to the IL-2 receptor, soluble TNF (tumor necrosis factor) receptor, the IL-1 antagonist, and the like to treat or prevent the above disorders or conditions.

The dose ranges for the administration of the purified, recombinant proteins described above (as well as antibodies to the human IL-12 beta2 receptor proteins and fragments thereof, and antibodies to the complex of this invention) may be determined by those of ordinary skill in the art without undue experimentation. In general, appropriate dosages are those which are large enough to produce the desired effect, for example, blocking the binding of endogenous IL-12 to its natural receptor. The dosage should not be so large as to cause adverse side effects, such as unwanted cross-reactions, anaphylactic reactions, and the like. Generally, the dosage will vary with the age, condition, sex and extent of disease in the patient, counter indications, if any, immune tolerance and other such variables, to be adjusted by the individual physician. The purified, recombinant proteins described above (as well as antibodies to the human IL-12 beta2 receptor proteins and fragments thereof, and antibodies to the complex of this invention) can be administered parenterally by injection or by gradual perfusion over time. They can be administered intravenously, intraperitoneally, intramuscularly, or subcutaneously.

Preparations for parenteral adminstration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, alcohol/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replinishers, electrolyte replinishers, such as those based on Ringer's dextrose, and the like. Preservatives and other additives may also be present, such as, for example, anti-micorbials, anti-oxidants, chelating agents, inert gases and the like. See, generally, *Remington's Pharmaceutical Science*, 16th Ed., Mack Eds., 1980.

Assays for Determining Whether a Given Compound Blocks IL-12 Activity

An aspect of the invention is the use of either the human IL-12 beta2 receptor protein or the complex of this invention as a screening agent for pharmaceuticals. In accordance with this invention, we can determine whether a given compound blocks human IL-12 activity or acts as an agonist of IL-12.

A biological activity of human IL-12 is the stimulation of the proliferation of activated T- and NK-cells. Proliferation of activated T-cells causes alloantigen-induced immune responses, such as allograft rejection (such as skin, kidney, and heart transplants) and graft-versus-host reaction in patients who have received bone marrow transplants. This biological activity of human IL-12 is mediated by the binding of the human IL-12 molecules to cell surface receptors on the activated T-cells.

A compound that blocks human IL-12 activity would, therefore, inhibit the proliferation of activated T-cells and would be useful to treat or prevent alloantigen induced immune responses.

In order to determine if a compound blocks human IL-12 activity, first, a plurality of cells having expressed on their surface either the human IL-12 beta2 receptor protein or a fragment thereof, or the complex of the invention, which cells proliferate in the presence of human IL-12, is provided. The human IL-12 beta2 receptor protein or a fragment thereof binds to human IL-12 with low binding affinity, but when complexed with human beta1 receptor protein forms a complex having high binding affinity for human IL-12. The complex of the invention binds to human IL-12 with high binding affinity and comprises a complex of (1) human IL-12 beta2 receptor protein, or a fragment thereof which when complexed with a human IL-12 beta1 receptor protein forms a complex having high binding affinity to human IL-12, and (2) human IL-12 beta1 receptor protein, or a fragment thereof which when complexed with a human IL-12 beta2 receptor protein forms a complex having high binding affinity to human IL-12. Second, the cells are contacted with human IL-12 and the given compound. Third, it is determined whether the presence of the given compound inhibits proliferation of the cells.

In order to determine if a compound is an agonist of human IL-12, first, a plurality of cells having expressed on their surface either the human IL-12 beta2 receptor protein or a fragment thereof, or the complex of the invention, and which cells proliferate in the presence of human IL-12, is provided. The human IL-12 beta2 receptor protein or a fragment thereof binds to human IL-12 with low binding affinity, but when complexed with human beta1 receptor protein forms a complex having high binding affinity for human IL-12. The complex of the invention binds to human IL-12 with high binding affinity and comprises a complex of (1) human IL-12 beta2 receptor protein, or a fragment thereof which when complexed with a human IL-12 beta1 receptor protein forms a complex having high binding affinity to human IL-12, and (2) human IL-12 beta1 receptor protein, or a fragment thereof which when complexed with a human IL-12 beta2 receptor protein forms a complex having high binding affinity to human IL-12. Second, the cells are contacted with human IL-12 or the given compound. Third, it is determined whether the presence of the given compound stimulates proliferation of the cells.

Examples of cells capable of expressing on their surface the complex, which cells proliferate in the presence of human IL-12 include, without limitation, PHA-activated PBMC, Kit 225/K6 cells, and Ba/F3 cells transfected with cDNA for both human IL-12 beta1 receptor protein and human IL-12 beta2 receptor protein. Examples of cells capable of expressing on their surface the human IL-12 beta2 receptor protein, or a fragment thereof, which cells proliferate in the presence of human IL-12 include, without limitation, Ba/F3 cells transfected with cDNA for human IL-12 beta2 receptor protein.

In order to determine whether the presence of the given compound inhibits proliferation of the cells, the following procedure may be carried out. The human IL-12 responsive cells, having expressed on their surface the human IL-12 beta2 receptor protein, or a fragment thereof, or the human IL-12 receptor complex of the invention, are plated into wells of a microtiter plate. Human IL-12 is then added to some wells of the microtiter plate (standard wells) and allowed to react with the cells. The compound to be tested is added either before or simultaneously with human IL-12 to different wells of the microtiter plate (sample wells) and allowed to react with the cells. Any solvent used must be non-toxic to the cell. The proliferation of the cells is then measured by known methods, for example, labeling the cells after contact with human IL-12 and the compound (such as by incorporation of tritiated thymidine into the replicating DNA), measuring the accumulation of cellular metabolites (such as lactic acid), and the like. The proliferation of the cells of the standard wells is compared to proliferation of the cells of the sample wells. If the cells of the sample wells proliferate significantly less than the cells of the standard wells, the compound blocks IL-12 activity.

In order to determine whether the presence of the given compound simulates proliferation of the cells, the following procedure may be carried out. The human IL-12 responsive cells having expressed on their surface the human IL-12 beta2 receptor protein, or a fragment thereof, or the human IL-12 receptor complex of the invention are plated into wells of a microtiter plate. Human IL-12 is then added to some wells of the microtiter plate (standard wells) and allowed to react with the cells. The compound to be tested is added to different wells of the microtiter plate (sample wells) and allowed to react with the cells. Any solvent used must be non-toxic to the cell. The proliferation of the cells is then measured by known methods, for example, labeling the cells after contact with the compound (such as by incorporation of tritiated thymidine into the replicating DNA), measuring the accumulation of cellular metabolites (such as lactic acid), and the like. The proliferation of the cells of the standard wells is compared to proliferation of the cells of the sample wells. If the cells of the sample wells proliferate significantly more than cells that were not exposed to human IL-12, the compound is an agonist of human IL-12.

The following examples are offered by way of illustration, not by limitation.

DETAILED DESCRIPTION OF THE PREFERRED EMBODIMENTS

MATERIALS

Proteins, Plasmids and Strains

Recombinant human IL-12 (U. Gubler et al., 1991, Proc. Natl. Acad. Sci. USA., 88:4143) was obtained as described therein.

Recombinant human IL-2 (H. W. Lahm et al., 1985, J. Chromatog, 326:357) was obtained as described therein The plasmid pEF-BOS was obtained from Dr. Nagata at the Osaka Bioscience Institute in Japan. The plasmid is based on a pUC 119 backbone and contains the elongation factor 1 alpha promoter to drive expression of genes inserted at the BstXI site (S. Mizushima and S. Nagata, Nucl. Acids Res., 1990, 18:5322).

The human IL-12 receptor beta1 cDNA in the plasmid pEF-BOS was obtained as described in A. Chua et al., 1994, J. Immunology 153:128 and in U.S. patent application Ser. No. 08/248,532, filed May 31, 1994, now U.S. Pat. No. 5,536,657.

Electrocompetent *E.coli* DH-10B (S. Grant et al., 1990, Proc. Natl. Acad. Sci USA 87:4645) was obtained from Bethesda Research Laboratory (Bethesda, Md.).

METHODS

Labeling of Human IL-12 With $^{125}$I

Recombinant human IL-12 was labeled with $^{125}$I as follows. Iodogen was dissolved in chloroform. 0.05 mg aliquots of Iodogen were dried in 12×150 mm borosilicate glass tubes. For radiolabeling, 1.0 mCi Na[$^{125}$I] was added to the Iodogen-coated borosilicate glass tube, which also contained 0.05 ml of Tris-iodination buffer (25 mM Tris-HCL pH 7.5, 0.4 M NaCl and 1 mM EDTA) to form a $^{125}$I solution. The $^{125}$I solution was activated by incubating for 6 minutes at room temperature. The activated $^{125}$I solution was transferred to a tube containing 0.05 to 0.1 ml recombinant human IL-12 (31.5 µg) in Tris-iodination buffer. The resulting mixture of the activated $^{125}$I solution and the recombinant human IL-12 was incubated for 6 minutes at room temperature. At the end of the incubation, 0.05 ml of Iodogen stop buffer (10 mg/ml tyrosine, 10% glycerol in Dulbecco's phosphate buffered saline (PBS), pH 7.40) was added and reacted for 3 minutes. The resulting mixture was then diluted with 1.0 ml Tris-iodination buffer containing 0.25% bovine serum albumin (BSA), and applied to a Bio-Gel P10DG desalting column for chromatography. The column was eluted with Tris-iodination buffer containing 0.25% BSA. 1 ml fractions containing the eluted peak amounts of labeled recombinant human IL-12 were combined. The combined fractions were diluted to 1×10$^8$ cpm/ml with 1% BSA in Tris-iodination buffer. Incorporation of $^{125}$I into recombinant human IL-12 was monitered by precipitation with trichloroacetic acid (TCA). The TCA precipitable radioactivity (10% TCA final concentration) was typically in excess of 95% of the total radioactivity. The radiospecific activity of the labeled recombinant human IL-12 was typically 1000 to 2000 cpm/fmole.

EXAMPLE 1

Preparation of Human PHA-activated Lymphoblasts

Human peripheral blood mononuclear cells (PBMC) were isolated from blood collected from healthy donors as described in Gately et al., J. Natl. Cancer Inst. 69, 1245 (1982). The blood was collected into heparinized syringes, diluted with an equal volume of Hank's balanced salt solution and layered over lymphocyte separation medium (LSM®) obtained from Organon Teknika Corporation, Durham, N.C.) in tubes. The tubes were spun at 2000 rpm for 20 minutes at room temperature. PBMC at the interface of the aqueous blood solution and the lymphocyte separation medium were collected. Collected PBMC were pelleted at 1500 rpm for 10 minutes through a 15 ml cushion of 20% sucrose in Hank's balanced salt solution. Pelleted PBMC were resuspended in tissue culture medium (1:1 mixture of RPMI 1640 and Dulbecco's modified Eagle's medium, supplemented with 0.1 mM nonessential amino acids, 60 μg/ml arginine HCl, 10 mM Hepes buffer, 2 μM L-glutamine, 100 U/ml penicillin, 100 μg/ml streptomycin, 0.05 mM 2-mercaptoethanol, and 1 μg/ml dextrose) (TCM) plus 5% human serum and washed twice in TCM.

The PBMC were then activated to form lymphoblasts. In particular, $0.5-1\times10^6$ cells/ml in TCM plus 5% human serum plus 0.1% (v/v) PHA-P (Difco, Detroit, Mich.) were cultured for 3 days at 37° C. in a 5% $CO_2$ atmosphere.

After three days, cell cultures were split 1:1 by volume in TCM plus 5% human serum and 50 U/ml recombinant human IL-2 to yield >95% T-cells. These cells were utilized for preparation of a cDNA library.

EXAMPLE 2

Extraction and Characterization of RNA

PBMC isolated as in Example 1, activated with PHA for 2–3 days, were harvested and total RNA was extracted using Guanidine Isothiocyanate/Phenol as described by P. Chomczynski and N. Sacchi, Anal. Biochem., 162:156, 1987. PolyA+ RNA was isolated from the total RNA by one batch adsorption to oligo dT latex beads as described (K. Kuribayashi et al., Nucl. Acids Res. Symposium Series 19:61, 1988). The mass yield of this purification was about 4% of polyA+ RNA.

EXAMPLE 3 cDNA Library

From the above polyA+ RNA, a cDNA library was established in the mammalian expression vector pEF-BOS as follows.

3 μg of polyA+ RNA were reverse transcribed into single stranded cDNAs using RNaseH minus reverse transcriptase in the presence of $\alpha$-$^{32}$P-dCTP. The resulting single stranded cDNAs were converted into blunt ended double stranded cDNAs as described by U. Gubler and A. Chua, Essential Molecular Biology Volume II, T. A. Brown, editor, pp. 39–56, IRL Press 1991. BstXI linkers (A. Aruffo and B. Seed, Proc. Natl. Acad. Sci (USA) 84, 8573, 1987) were ligated to the resulting double stranded cDNAs.

cDNA molecules having a size of greater than 800 base pairs (bp) were selected by size exclusion chromatography as follows. A Sephacryl SF 500 column (0.8×29 cm) was packed by gravity in 10 mM Tris-HCl pH 7.8—1 mM EDTA—100 mM NaAcetate. The radioactive cDNA with added BstXI linkers was applied to the column and 0.5 ml fractions were collected. The size distribution of radioactive cDNA was determined by performing electrophoresis on a small aliquot of each fraction on a 1% agarose gel, drying the gel, and visualizing the size by exposure of the gel to X-ray film. cDNA molecules larger than 800 bp were size selected in this fashion.

The selected cDNA molecules were pooled and concentrated by ethanol precipitation. The pooled and concentrated selected cDNA molecules were subsequently ligated to the plasmid pEF-BOS as follows. The plasmid had been restricted with BstXI and purified over two consecutive 1% agarose gels. 300 ng of the restricted and purified plasmid DNA were ligated to 30 ng of size selected cDNA in 60 μl of ligation buffer (50 mM Tris-HCl pH 7.8—10 mM $MgCl_2$—10 mM DTT—1 mM rATP—25 mg/ml BSA) at 15° C. overnight.

The following day, the plasmid ligated with the size selected cDNA was extracted with phenol. 6 mg of mussel glycogen were added to the resulting extract, and the nucleic acids were precipitated by ethanol. The resulting precipitate was dissolved in water and the nucleic acids again were precipitated by ethanol, followed by a wash with 80% ethanol. A pellet was formed from the precipitated and washed nucleic acids. The pellet was dissolved in 6 μl of water. 1 μl aliquots of the dissolved pellet were subsequently electroporated into E.Coli strain DH-10B. Upon electroporated of 5 parallel aliquots, a library of about 10 million recombinants was generated.

EXAMPLE 4

Expression Screening for cDNAs Encoding High Affinity IL-12 Receptors

The library was screened according to the general expression screening method described by Hara and Miyajima, 1992, EMBO, 11:1875.

Pools of about 100 E.coli clones from the above library were grown and the plasmid DNA was extracted from the pools by conventional methods. $2\times10^5$ COS cells were plated per 35 mm culture well. COS cells were transfected with a transfection cocktail using the standard DEAE dextran technique described in "Molecular Cloning, a Laboratory Manual", 2nd Ed., J. Sambrook et al., Cold Spring Harbor Laboratory Press, 1989 ("Molecular Cloning"). The transfection cocktail contained (1) 1 μg of plasmid DNA extracted from the E.coli clone pools derived from the above library, and (2) 0.1 μg of pEF-BOS plasmid DNA containing the human IL-12 receptor beta1 cDNA.

3 days after transfection, the wells of COS cells were incubated with 10 pM labeled human recombinant IL-12 (specific activity=1000–2000 cpm/fmole) for 90 minutes at room temperature. The labeled human recombinant IL-12 was removed, and the COS cell monolayer was washed for one hour three times with binding buffer (RPMI 1640, 5% fetal bovine serum (FBS), 25 mM HEPES pH 7) to further select for COS cells expressing high affinity IL-12 receptors only (the binding of the IL-12 ligand to the low affinity sites was further reduced because the low affinity sites have a higher dissociation rate). Subsequently, the cell monolayers were lysed and counted in a gamma counter. After screening 440 pools (representing about 44,000 clones), one pool consistently showed a positive binding signal (300 cpm over 100 cpm background). From this pool, a single clone was subsequently isolated by sib-selection. This single clone (B5-10) contained a cDNA insert of about 3 kb that was completely sequenced.

The cDNA insert of clone B5-10 was incomplete with regard to the protein coding region because it did not contain an in-frame stop codon. The cDNA library of Example 3 was rescreened by conventional DNA hybridization techniques with the cDNA insert from clone B5-10, as described in Molecular Cloning and by Grunstein and Hogness, 1975, Proc. Nat. Acad. Sci. USA., 72:3961. Additional clones were thus isolated and then partially sequenced. The nucleotide sequence of one clone (No. 3) was found to (i) overlap with the 3' end of the nucleotide sequence of clone B5-10, (ii) extend beyond the nucleotide sequence of clone B5-10, and (iii) contain an in-frame stop codon.

This composite DNA sequence is shown in SEQ ID NO:1. The deduced amino acid sequence for the encoded receptor protein is shown in SEQ ID NO:2. Based on the previously suggested nomenclature of Stahl and Yancopolous, 1993, Cell 74:587, we call this newly isolated human IL-12 receptor chain the beta2 chain.

EXAMPLE 5

Binding Assays

COS cells (4–5×10$^7$) were transfected by electroporation using a BioRad Gene Pulser (250 μF, 250 volts) with either (1) 25 μg of the B5-10 plasmid DNA expressing recombinant human IL-12 beta2 receptor protein, (2) 25 μg of the pEF-BOS plasmid DNA expressing recombinant human IL-12 beta1 receptor protein, or (3) a mixture of 12.5 μg of the B5-10 plasmid DNA expressing recombinant human IL-12 beta2 receptor protein and 12.5 μg of the pEF-BOS plasmid DNA expressing recombinant human IL-12 beta1 receptor protein. The electroporated cells were plated in a 600 cm$^2$ culture plate, harvested after 72 hours by scraping, washed and resuspended in binding buffer.

The cells were assayed to determine affinities of the expressed IL-12 receptors for human IL-12. In particular, equilibrium binding of labeled recombinant human IL-12 to the cells was performed and analyzed as described by R. Chizzonite, et al., 1992, J. Immunol., 148:3117. Electroporated cells (8×10$^4$) were incubated with increasing concentrations of $^{125}$I-labeled recombinant human IL-12 at room temperature for 2 hours. Incubations were carried out in duplicate or triplicate.

Cell bound radioactivity was separated from free labeled $^{125}$I-IL-12 by centrifugation of the mixture of electroporated cells and $^{125}$I-labeled recombinant human IL-12 through 0.1 ml of an oil mixture (1:2 mixture of Thomas Silicone Fluid 6428-R15 {A. H. Thomas} and Silicone Oil AR 200 {Gallard-Schlessinger}) at 4° C. for 90 seconds at 10,000×g to form a cell pellet in a tube. The cell pellet was excised from the tip of the tube in which it was formed, and cell bound radioactivity was determined in a gamma counter.

Receptor binding data were analyzed and the affinities were calculated according to Scatchard using the method described by McPherson, J., 1985, Pharmacol. Methods, 14:213.

EXAMPLE 6

Production of IL-12 Responsive Cell Line

Wild-type Ba/F3 cells, an IL-3-dependent mouse pro-B cell (Palacios, R. et al., 1985, Cell 41:727) and Ba/F3 cells expressing human IL-12 beta1 receptor protein (Chua, A., et al., 1994, J. Imunology 153:128) were cotransfected with (1) 80 μg of pEF-BOS plasmid DNA expressing recombinant human IL-12 beta2 receptor protein and (2) 8 μg of a plasmid expressing a hygromycin resistance gene (Giordano, T. J., et al., 1990, Gene 88:285) by electroporation using a BioRad Gene Pulser (960 μF, 400 volts).

All cells were resuspended at a density of 2×10$^5$ viable cells/ml in a growth medium of RPMI 1640, 10% FBS, glutamine (2 mM), penicillin G (100 U/ml), streptomycin (100 μg/ml), and 10% conditioned medium from the WEHI-3 cell line (ATCC No. TIB 68, American Type Culture Collection, Rockville, Md.). The WEHI-3 cell line is a source of IL-3. The resuspended cells were then incubated at 37° C. under 5% CO$_2$ for 120 hours.

Cells were selected by their ability to grow in (1) the above growth medium in the presence of 1 mg/ml hygromycin or (2) an IL-12 containing growth medium of RPMI 1640, 10% FBS, glutamine (2 mM), penicillin G (100 U/ml), streptomycin (100 μg/ml), and various concentrations (10, 50 or 250 ng/ml) of human IL-12.

Ba/F3 cells expressing human IL-12 beta1 receptor protein transfected with pEF-BOS plasmid DNA expressing recombinant human IL-12 beta2 receptor protein grew in the IL-12 containing growth medium, demonstrating that coexpression of human IL-12 beta1 receptor protein and human IL-12 beta2 receptor protein conferred human IL-12 responsiveness to the Ba/F3 cells.

Additionally, Ba/F3 cells expressing human IL-12 beta2 receptor protein grow in the IL-12 containing growth medium, demonstrating that expression of human IL-12 beta2 receptor protein conferred human IL-12 responsiveness to the Ba/F3 cells.

Effect of Human IL-12 on Transfected Ba/F3 Cell Lines

Ba/F3 cells (1) expressing human IL-12 beta1 receptor protein, (2) expressing human IL-12 beta2 receptor protein, or (3) coexpressing human IL-12 beta1 receptor protein and human IL-12 beta2 receptor protein were cultured in RPMI-1640 medium supplemented with 10% FBS, 100 U/ml penicillin G, 100 μg/ml streptomycin, and 2 mM L-glutamine at 2×10$^4$ cells/well in Costar 3596 flat-bottom microplates for 24 hours. Various dilutions of human IL-12, as shown in FIG. 6, were then added to the microplates and the cells were incubated for 42 hours at 37° C. in a humidified atmosphere of 5% CO$_2$ in air. 50 μl of $^3$H-thymidine, 10 μCi/ml in culture medium, was then added to each well. The cultures were further incubated for 6 hours at 37° C. Subsequently, the culture contents were harvested onto glass fiber filters by means of a cell harvester. $^3$H-thymidine incorporation was measured by use of a liquid scintillation counter. All samples were assayed in quadruplicate.

Results

Sequence Analysis of IL-12 Receptor cDNA Clones and Encoded IL-12 Receptor Protein The IL-12 beta2 receptor protein, composed of 862 amino acids and a calculated molecular weight of 97231, had the following features: N-terminal signal peptide, extracellular domain, transmembrane domain and cytoplasmic tail. The classical hydrophobic N-terminal signal peptide is predicted to be 23 amino acids in length. Signal peptide cleavage occurs mostly after the amino acids Ala, Ser, Gly, Cys, Thr, Gln (von Heijne, G., 1986, Nucl. Acids Research, 14:4683). For the IL-12 receptor, the cleavage could thus take place after Ala23 in the sequence shown in SEQ ID NO:2, leaving a mature protein of 839 amino acids based on cleavage at Ala23. The extracellular domain of the receptor is predicted to encompass the region from the C-terminus of the signal peptide to amino acid No. 622 in the sequence shown in SEQ ID NO:2. Hydrophobicity analysis shows the area from amino acid No. 623 to 646 to be hydrophobic, as would be expected for a transmembrane anchor region. Charged transfer stop residues can be found at the N- as well as the C-terminus of this predicted transmembrane area. The extracellular domain of the receptor is thus 599 amino acids long and contains 9 predicted N-linked glycosylation sites. The cytoplasmic portion is 215 amino acids long (amino acid residue nos. 647 to 862).

Further analysis of the amino acid sequence shown in SEQ ID NO:2 shows the human IL-12 beta2 receptor protein is a member of the cytokine receptor superfamily, by virtue of the sequence motifs [Cys132 - - - Cys143TW] and [W305SKWS]. Comparing the sequence shown in SEQ ID NO:2 to all the members of the superfamily by running the ALIGN program shows that the human IL-12 beta2 receptor protein has the highest homology to human gp130. The cytoplasmic region of the IL-12 receptor beta2 chain contains the box 1 and 2 motifs found in other cytokine receptor superfamily members, as well as three tyrosine residues. Phosphorylation of tyrosines is commonly associated with cytokine receptor signalling; the presence of these tyrosine residues underscores the importance of the IL-12 receptor beta2 chain in the formation of a functional IL-12 receptor. The IL-12 receptor beta1 chain does not contain any tyrosine residues in its cytoplasmic tail.

Binding Assays

We have found that human IL-12 binds to recombinant IL-12 receptor beta1 or beta2 alone with an apparent affinity of about 2–5 nM. The binding data was described by a single site receptor model, corresponding to the low affinity component of the functional IL-12 receptor found on PHA-activated PBMC (R. Chizzonite et al., 1992, J. Immunol., 148:3117; B. Desai et al., 1992, J. Immunol., 148:3125).

In contrast to these results, both high and low affinity IL-12 binding sites were generated upon cotransfection of COS cells with IL-12 receptor beta1 and beta2 plasmids. In this case, the binding data were described by a two receptor site model, with affinities of 50 pM and 5 nM.

Effect of Human IL-12 on Transfected Ba/F3 Cell Lines

We conducted a proliferation assay for the effect of human IL-12 on Ba/F3 cells (1) expressing human IL-12 beta1 receptor protein, (2) expressing human IL-12 beta2 receptor protein, and (3) coexpressing human IL-12 beta1 receptor protein and human IL-12 beta2 receptor protein We have found that cells that are transfected with cDNAs for both human IL-12 beta1 receptor protein and human IL-12 beta2 receptor protein respond to stimulation by human IL-12 by proliferating in a dose-dependent manner.

Additionally, we have found that cells that are transfected with cDNAs for human IL-12 beta2 receptor protein respond to stimulation by human IL-12 by proliferating in a dose-dependent manner.

Conclusion

The isolated cDNA (clone No. B5-10, SEQ ID No:1) coding for a type I transmembrane protein represents a second component of the IL-12 receptor (IL-12R beta2) found on normal human T-cells. The beta1 and beta2 chains each alone bind IL-12 only with low affinity (Kd=2–5 nM). Upon coexpression of beta1 and beta2, two affinity sites are observed, with Kd values of 50 pM and 5 nM.

Ba/F3 cells expressing human IL-12 beta2 receptor protein or coexpressing human IL-12 beta1 receptor protein and human IL-12 beta2 receptor protein are responsive to human IL-12.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A human interleukin-12 (IL-12) beta2 receptor protein which has the amino acid sequence SEQ ID NO:2, or a protein which has an amino acid sequence which is encoded by a nucleic acid sequence which hybridizes under stringent conditions to the nucleic acid sequence which encodes SEQ ID NO:2, which protein (a) has low binding affinity for human IL-12, and (b) when complexed with a human IL-12 beta1 receptor protein forms a complex having high binding affinity to human IL-12, the protein being free from other human proteins.

2. The human IL-12 beta2 receptor protein of claim 1, having SEQ ID NO:2.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 4040 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 641..3226

(xi) SEQUENCE DESCRIPTION: SEQ ID NO:1:

```
TGCAGAGAAC AGAGAAAGGA CATCTGCGAG GAAAGTTCCC TGATGGCTGT CAACAAAGTG      60

CCACGTCTCT ATGGCTGTGT ACGCTGAGCA CACGATTTTA TCGCGCCTAT CATATCTTGG     120

TGCATAAACG CACCTCACCT CGGTCAACCC TTGCTCCGTC TTATGAGACA GGCTTTATTA     180

TCCGCATTTT ATATGAGGGG AATCTGACGG TGGAGAGAGA ATTATCTTGC TCAAGGCGAC     240

ACAGCAGAGC CCACAGGTGG CAGAATCCCA CCCGAGCCCG CTTCGACCCG CGGGGTGGAA     300

ACCACGGGCG CCCGCCCGGC TGCGCTTCCA GAGCTGAACT GAGAAGCGAG TCCTCTCCGC     360
```

```
CCTGCGGCCA CCGCCCAGCC CCGACCCCCG CCCCGGCCCG ATCCTCACTC GCCGCCAGCT      420

CCCCGCGCCC ACCCCGGAGT TGGTGGCGCA GAGGCGGGAG GCGGAGGCGG GAGGGCGGGC      480

GCTGGCACCG GGAACGCCCG AGCGCCGGCA GAGAGCGCGG AGAGCGCGAC ACGTGCGGCC      540

CAGAGCACCG GGGCCACCCG GTCCCCGCAG GCCCGGGACC GCGCCCGCTG GCAGGCGACA      600

CGTGGAAGAA TACGGAGTTC TATACCAGAG TTGATTGTTG ATG GCA CAT ACT TTT        655
                                             Met Ala His Thr Phe
                                              1               5

AGA GGA TGC TCA TTG GCA TTT ATG TTT ATA ATC ACG TGG CTG TTG ATT        703
Arg Gly Cys Ser Leu Ala Phe Met Phe Ile Ile Thr Trp Leu Leu Ile
                10              15              20

AAA GCA AAA ATA GAT GCG TGC AAG AGA GGC GAT GTG ACT GTG AAG CCT        751
Lys Ala Lys Ile Asp Ala Cys Lys Arg Gly Asp Val Thr Val Lys Pro
            25              30              35

TCC CAT GTA ATT TTA CTT GGA TCC ACT GTC AAT ATT ACA TGC TCT TTG        799
Ser His Val Ile Leu Leu Gly Ser Thr Val Asn Ile Thr Cys Ser Leu
        40              45              50

AAG CCC AGA CAA GGC TGC TTT CAC TAT TCC AGA CGT AAC AAG TTA ATC        847
Lys Pro Arg Gln Gly Cys Phe His Tyr Ser Arg Arg Asn Lys Leu Ile
    55              60              65

CTG TAC AAG TTT GAC AGA AGA ATC AAT TTT CAC CAT GGC CAC TCC CTC        895
Leu Tyr Lys Phe Asp Arg Arg Ile Asn Phe His His Gly His Ser Leu
70              75              80              85

AAT TCT CAA GTC ACA GGT CTT CCC CTT GGT ACA ACC TTG TTT GTC TGC        943
Asn Ser Gln Val Thr Gly Leu Pro Leu Gly Thr Thr Leu Phe Val Cys
            90              95              100

AAA CTG GCC TGT ATC AAT AGT GAT GAA ATT CAA ATA TGT GGA GCA GAG        991
Lys Leu Ala Cys Ile Asn Ser Asp Glu Ile Gln Ile Cys Gly Ala Glu
        105             110             115

ATC TTC GTT GGT GTT GCT CCA GAA CAG CCT CAA AAT TTA TCC TGC ATA       1039
Ile Phe Val Gly Val Ala Pro Glu Gln Pro Gln Asn Leu Ser Cys Ile
    120             125             130

CAG AAG GGA GAA CAG GGG ACT GTG GCC TGC ACC TGG GAA AGA GGA CGA       1087
Gln Lys Gly Glu Gln Gly Thr Val Ala Cys Thr Trp Glu Arg Gly Arg
135             140             145

GAC ACC CAC TTA TAC ACT GAG TAT ACT CTA CAG CTA AGT GGA CCA AAA       1135
Asp Thr His Leu Tyr Thr Glu Tyr Thr Leu Gln Leu Ser Gly Pro Lys
150             155             160             165

AAT TTA ACC TGG CAG AAG CAA TGT AAA GAC ATT TAT TGT GAC TAT TTG       1183
Asn Leu Thr Trp Gln Lys Gln Cys Lys Asp Ile Tyr Cys Asp Tyr Leu
        170             175             180

GAC TTT GGA ATC AAC CTC ACC CCT GAA TCA CCT GAA TCC AAT TTC ACA       1231
Asp Phe Gly Ile Asn Leu Thr Pro Glu Ser Pro Glu Ser Asn Phe Thr
    185             190             195

GCC AAG GTT ACT GCT GTC AAT AGT CTT GGA AGC TCC TCT TCA CTT CCA       1279
Ala Lys Val Thr Ala Val Asn Ser Leu Gly Ser Ser Ser Ser Leu Pro
200             205             210

TCC ACA TTC ACA TTC TTG GAC ATA GTG AGG CCT CTT CCT CCG TGG GAC       1327
Ser Thr Phe Thr Phe Leu Asp Ile Val Arg Pro Leu Pro Pro Trp Asp
    215             220             225

ATT AGA ATC AAA TTT CAA AAG GCT TCC GTG AGC AGA TGT ACC CTT TAT       1375
Ile Arg Ile Lys Phe Gln Lys Ala Ser Val Ser Arg Cys Thr Leu Tyr
230             235             240             245

TGG AGA GAT GAG GGA CTG GTA CTG CTT AAT CGA CTC AGA TAT CGG CCC       1423
Trp Arg Asp Glu Gly Leu Val Leu Leu Asn Arg Leu Arg Tyr Arg Pro
        250             255             260

AGT AAC AGC AGG CTC TGG AAT ATG GTT AAT GTT ACA AAG GCC AAA GGA       1471
Ser Asn Ser Arg Leu Trp Asn Met Val Asn Val Thr Lys Ala Lys Gly
    265             270             275
```

```
AGA CAT GAT TTG CTG GAT CTG AAA CCA TTT ACA GAA TAT GAA TTT CAG      1519
Arg His Asp Leu Leu Asp Leu Lys Pro Phe Thr Glu Tyr Glu Phe Gln
        280                 285                 290

ATT TCC TCT AAG CTA CAT CTT TAT AAG GGA AGT TGG AGT GAT TGG AGT      1567
Ile Ser Ser Lys Leu His Leu Tyr Lys Gly Ser Trp Ser Asp Trp Ser
    295                 300                 305

GAA TCA TTG AGA GCA CAA ACA CCA GAA GAA GAG CCT ACT GGG ATG TTA      1615
Glu Ser Leu Arg Ala Gln Thr Pro Glu Glu Glu Pro Thr Gly Met Leu
310                 315                 320                 325

GAT GTC TGG TAC ATG AAA CGG CAC ATT GAC TAC AGT AGA CAA CAG ATT      1663
Asp Val Trp Tyr Met Lys Arg His Ile Asp Tyr Ser Arg Gln Gln Ile
                330                 335                 340

TCT CTT TTC TGG AAG AAT CTG AGT GTC TCA GAG GCA AGA GGA AAA ATT      1711
Ser Leu Phe Trp Lys Asn Leu Ser Val Ser Glu Ala Arg Gly Lys Ile
            345                 350                 355

CTC CAC TAT CAG GTG ACC TTG CAG GAG CTG ACA GGA GGG AAA GCC ATG      1759
Leu His Tyr Gln Val Thr Leu Gln Glu Leu Thr Gly Gly Lys Ala Met
        360                 365                 370

ACA CAG AAC ATC ACA GGA CAC ACC TCC TGG ACC ACA GTC ATT CCT AGA      1807
Thr Gln Asn Ile Thr Gly His Thr Ser Trp Thr Thr Val Ile Pro Arg
    375                 380                 385

ACC GGA AAT TGG GCT GTG GCT GTG TCT GCA GCA AAT TCA AAA GGC AGT      1855
Thr Gly Asn Trp Ala Val Ala Val Ser Ala Ala Asn Ser Lys Gly Ser
390                 395                 400                 405

TCT CTG CCC ACT CGT ATT AAC ATA ATG AAC CTG TGT GAG GCA GGG TTG      1903
Ser Leu Pro Thr Arg Ile Asn Ile Met Asn Leu Cys Glu Ala Gly Leu
                410                 415                 420

CTG GCT CCT CGC CAG GTC TCT GCA AAC TCA GAG GGC ATG GAC AAC ATT      1951
Leu Ala Pro Arg Gln Val Ser Ala Asn Ser Glu Gly Met Asp Asn Ile
            425                 430                 435

CTG GTG ACT TGG CAG CCT CCC AGG AAA GAT CCC TCT GCT GTT CAG GAG      1999
Leu Val Thr Trp Gln Pro Pro Arg Lys Asp Pro Ser Ala Val Gln Glu
        440                 445                 450

TAC GTG GTG GAA TGG AGA GAG CTC CAT CCA GGG GGT GAC ACA CAG GTC      2047
Tyr Val Val Glu Trp Arg Glu Leu His Pro Gly Gly Asp Thr Gln Val
    455                 460                 465

CCT CTA AAC TGG CTA CGG AGT CGA CCC TAC AAT GTG TCT GCT CTG ATT      2095
Pro Leu Asn Trp Leu Arg Ser Arg Pro Tyr Asn Val Ser Ala Leu Ile
470                 475                 480                 485

TCA GAG AAC ATA AAA TCC TAC ATC TGT TAT GAA ATC CGT GTG TAT GCA      2143
Ser Glu Asn Ile Lys Ser Tyr Ile Cys Tyr Glu Ile Arg Val Tyr Ala
                490                 495                 500

CTC TCA GGG GAT CAA GGA GGA TGC AGC TCC ATC CTG GGT AAC TCT AAG      2191
Leu Ser Gly Asp Gln Gly Gly Cys Ser Ser Ile Leu Gly Asn Ser Lys
            505                 510                 515

CAC AAA GCA CCA CTG AGT GGC CCC CAC ATT AAT GCC ATC ACA GAG GAA      2239
His Lys Ala Pro Leu Ser Gly Pro His Ile Asn Ala Ile Thr Glu Glu
        520                 525                 530

AAG GGG AGC ATT TTA ATT TCA TGG AAC AGC ATT CCA GTC CAG GAG CAA      2287
Lys Gly Ser Ile Leu Ile Ser Trp Asn Ser Ile Pro Val Gln Glu Gln
    535                 540                 545

ATG GGC TGC CTC CTC CAT TAT AGG ATA TAC TGG AAG GAA CGG GAC TCC      2335
Met Gly Cys Leu Leu His Tyr Arg Ile Tyr Trp Lys Glu Arg Asp Ser
550                 555                 560                 565

AAC TCC CAG CCT CAG CTC TGT GAA ATT CCC TAC AGA GTC TCC CAA AAT      2383
Asn Ser Gln Pro Gln Leu Cys Glu Ile Pro Tyr Arg Val Ser Gln Asn
                570                 575                 580

TCA CAT CCA ATA AAC AGC CTG CAG CCC CGA GTG ACA TAT GTC CTG TGG      2431
Ser His Pro Ile Asn Ser Leu Gln Pro Arg Val Thr Tyr Val Leu Trp
            585                 590                 595
```

| | | |
|---|---|---|
| ATG ACA GCT CTG ACA GCT GCT GGT GAA AGT TCC CAC GGA AAT GAG AGG<br>Met Thr Ala Leu Thr Ala Ala Gly Glu Ser Ser His Gly Asn Glu Arg<br>600 605 610 | | 2479 |
| GAA TTT TGT CTG CAA GGT AAA GCC AAT TGG ATG GCG TTT GTG GCA CCA<br>Glu Phe Cys Leu Gln Gly Lys Ala Asn Trp Met Ala Phe Val Ala Pro<br>615 620 625 | | 2527 |
| AGC ATT TGC ATT GCT ATC ATC ATG GTG GGC ATT TTC TCA ACG CAT TAC<br>Ser Ile Cys Ile Ala Ile Ile Met Val Gly Ile Phe Ser Thr His Tyr<br>630 635 640 645 | | 2575 |
| TTC CAG CAA AAG GTG TTT GTT CTC CTA GCA GCC CTC AGA CCT CAG TGG<br>Phe Gln Gln Lys Val Phe Val Leu Leu Ala Ala Leu Arg Pro Gln Trp<br>650 655 660 | | 2623 |
| TGT AGC AGA GAA ATT CCA GAT CCA GCA AAT AGC ACT TGC GCT AAG AAA<br>Cys Ser Arg Glu Ile Pro Asp Pro Ala Asn Ser Thr Cys Ala Lys Lys<br>665 670 675 | | 2671 |
| TAT CCC ATT GCA GAG GAG AAG ACA CAG CTG CCC TTG GAC AGG CTC CTG<br>Tyr Pro Ile Ala Glu Glu Lys Thr Gln Leu Pro Leu Asp Arg Leu Leu<br>680 685 690 | | 2719 |
| ATA GAC TGG CCC ACG CCT GAA GAT CCT GAA CCG CTG GTC ATC AGT GAA<br>Ile Asp Trp Pro Thr Pro Glu Asp Pro Glu Pro Leu Val Ile Ser Glu<br>695 700 705 | | 2767 |
| GTC CTT CAT CAA GTG ACC CCA GTT TTC AGA CAT CCC CCC TGC TCC AAC<br>Val Leu His Gln Val Thr Pro Val Phe Arg His Pro Pro Cys Ser Asn<br>710 715 720 725 | | 2815 |
| TGG CCA CAA AGG GAA AAA GGA ATC CAA GGT CAT CAG GCC TCT GAG AAA<br>Trp Pro Gln Arg Glu Lys Gly Ile Gln Gly His Gln Ala Ser Glu Lys<br>730 735 740 | | 2863 |
| GAC ATG ATG CAC AGT GCC TCA AGC CCA CCA CCT CCA AGA GCT CTC CAA<br>Asp Met Met His Ser Ala Ser Ser Pro Pro Pro Pro Arg Ala Leu Gln<br>745 750 755 | | 2911 |
| GCT GAG AGC AGA CAA CTG GTG GAT CTG TAC AAG GTG CTG GAG AGC AGG<br>Ala Glu Ser Arg Gln Leu Val Asp Leu Tyr Lys Val Leu Glu Ser Arg<br>760 765 770 | | 2959 |
| GGC TCC GAC CCA AAG CCA GAA AAC CCA GCC TGT CCC TGG ACG GTG CTC<br>Gly Ser Asp Pro Lys Pro Glu Asn Pro Ala Cys Pro Trp Thr Val Leu<br>775 780 785 | | 3007 |
| CCA GCA GGT GAC CTT CCC ACC CAT GAT GGC TAC TTA CCC TCC AAC ATA<br>Pro Ala Gly Asp Leu Pro Thr His Asp Gly Tyr Leu Pro Ser Asn Ile<br>790 795 800 805 | | 3055 |
| GAT GAC CTC CCC TCA CAT GAG GCA CCT CTC GCT GAC TCT CTG GAA GAA<br>Asp Asp Leu Pro Ser His Glu Ala Pro Leu Ala Asp Ser Leu Glu Glu<br>810 815 820 | | 3103 |
| CTG GAG CCT CAG CAC ATC TCC CTT TCT GTT TTC CCC TCA AGT TCT CTT<br>Leu Glu Pro Gln His Ile Ser Leu Ser Val Phe Pro Ser Ser Ser Leu<br>825 830 835 | | 3151 |
| CAC CCA CTC ACC TTC TCC TGT GGT GAT AAG CTG ACT CTG GAT CAG TTA<br>His Pro Leu Thr Phe Ser Cys Gly Asp Lys Leu Thr Leu Asp Gln Leu<br>840 845 850 | | 3199 |
| AAG ATG AGG TGT GAC TCC CTC ATG CTC TGAGTGGTGA GGCTTCAAGC<br>Lys Met Arg Cys Asp Ser Leu Met Leu<br>855 860 | | 3246 |
| CTTAAAGTCA GTGTGCCCTC AACCAGCACA GCCTGCCCCA ATTCCCCCAG CCCCTGCTCC | | 3306 |
| AGCAGCTGTC ATCTCTGGGT GCCACCATCG GTCTGGCTGC AGCTAGAGGA CAGGCAAGCC | | 3366 |
| AGCTCTGGGG GAGTCTTAGG AACTGGGAGT TGGTCTTCAC TCAGATGCCT CATCTTGCCT | | 3426 |
| TTCCCAGGGC CTTAAAATTA CATCCTTCAC TGTGTGGACC TAGAGACTCC AACTTGAATT | | 3486 |
| CCTAGTAACT TTCTTGGTAT GCTGGCCAGA AAGGGAAATG AGGAGGAGAG TAGAAACCAC | | 3546 |
| AGCTCTTAGT AGTAATGGCA TACAGTCTAG AGGACCATTC ATGCAATGAC TATTTCTAAA | | 3606 |

```
GCACCTGCTA CACAGCAGGC TGTACACAGC AGATCAGTAC TGTTCAACAG AACTTCCTGA    3666

GATGATGGAA ATGTTCTACC TCTGCACTCA CTGTCCAGTA CATTAGACAC TAGGCACATT    3726

GGCTGTTAAT CACTTGGAAT GTGTTTAGCT TGACTGAGGA ATTAAATTTT GATTGTAAAT    3786

TTAAATCGCC ACACATGGCT AGTGGCTACT GTATTGGAGT GCACAGCTCT AGATGGCTCC    3846

TAGATTATTG AGAGCCTCCA AAACAAATCA ACCTAGTTCT ATAGATGAAG ACATAAAAGA    3906

CACTGGTAAA CACCAATGTA AAAGGGCCCC CAAGGTGGTC ATGACTGGTC TCATTTGCAG    3966

AAGTCTAAGA ATGTACCTTT TTCTGGCCGG GCGTGGTAGC TCATGCCTGT AATCCCAGCA    4026

CTTTGGGAGG CTGA                                                      4040
```

(2) INFORMATION FOR SEQ ID NO:2:

(i) SEQUENCE CHARACTERISTICS:
        (A) LENGTH: 862 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala His Thr Phe Arg Gly Cys Ser Leu Ala Phe Met Phe Ile Ile
 1               5                  10                  15

Thr Trp Leu Leu Ile Lys Ala Lys Ile Asp Ala Cys Lys Arg Gly Asp
            20                  25                  30

Val Thr Val Lys Pro Ser His Val Ile Leu Leu Gly Ser Thr Val Asn
        35                  40                  45

Ile Thr Cys Ser Leu Lys Pro Arg Gln Gly Cys Phe His Tyr Ser Arg
    50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
            100                 105                 110

Ile Cys Gly Ala Glu Ile Phe Val Gly Val Ala Pro Glu Gln Pro Gln
        115                 120                 125

Asn Leu Ser Cys Ile Gln Lys Gly Glu Gln Gly Thr Val Ala Cys Thr
    130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
        195                 200                 205

Ser Ser Ser Leu Pro Ser Thr Phe Thr Phe Leu Asp Ile Val Arg Pro
    210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
```

-continued

```
                275                 280                 285
Glu Tyr Glu Phe Gln Ile Ser Ser Lys Leu His Leu Tyr Lys Gly Ser
            290                 295                 300
Trp Ser Asp Trp Ser Glu Ser Leu Arg Ala Gln Thr Pro Glu Glu
305                 310                 315                 320
Pro Thr Gly Met Leu Asp Val Trp Tyr Met Lys Arg His Ile Asp Tyr
                325                 330                 335
Ser Arg Gln Gln Ile Ser Leu Phe Trp Lys Asn Leu Ser Val Ser Glu
                340                 345                 350
Ala Arg Gly Lys Ile Leu His Tyr Gln Val Thr Leu Gln Glu Leu Thr
                355                 360                 365
Gly Gly Lys Ala Met Thr Gln Asn Ile Thr Gly His Thr Ser Trp Thr
370                 375                 380
Thr Val Ile Pro Arg Thr Gly Asn Trp Ala Val Ala Val Ser Ala Ala
385                 390                 395                 400
Asn Ser Lys Gly Ser Ser Leu Pro Thr Arg Ile Asn Ile Met Asn Leu
                405                 410                 415
Cys Glu Ala Gly Leu Leu Ala Pro Arg Gln Val Ser Ala Asn Ser Glu
                420                 425                 430
Gly Met Asp Asn Ile Leu Val Thr Trp Gln Pro Pro Arg Lys Asp Pro
                435                 440                 445
Ser Ala Val Gln Glu Tyr Val Val Glu Trp Arg Glu Leu His Pro Gly
450                 455                 460
Gly Asp Thr Gln Val Pro Leu Asn Trp Leu Arg Ser Arg Pro Tyr Asn
465                 470                 475                 480
Val Ser Ala Leu Ile Ser Glu Asn Ile Lys Ser Tyr Ile Cys Tyr Glu
                485                 490                 495
Ile Arg Val Tyr Ala Leu Ser Gly Asp Gln Gly Gly Cys Ser Ser Ile
                500                 505                 510
Leu Gly Asn Ser Lys His Lys Ala Pro Leu Ser Gly Pro His Ile Asn
                515                 520                 525
Ala Ile Thr Glu Glu Lys Gly Ser Ile Leu Ile Ser Trp Asn Ser Ile
                530                 535                 540
Pro Val Gln Glu Gln Met Gly Cys Leu Leu His Tyr Arg Ile Tyr Trp
545                 550                 555                 560
Lys Glu Arg Asp Ser Asn Ser Gln Pro Gln Leu Cys Glu Ile Pro Tyr
                565                 570                 575
Arg Val Ser Gln Asn Ser His Pro Ile Asn Ser Leu Gln Pro Arg Val
                580                 585                 590
Thr Tyr Val Leu Trp Met Thr Ala Leu Thr Ala Ala Gly Glu Ser Ser
                595                 600                 605
His Gly Asn Glu Arg Glu Phe Cys Leu Gln Gly Lys Ala Asn Trp Met
610                 615                 620
Ala Phe Val Ala Pro Ser Ile Cys Ile Ala Ile Met Val Gly Ile
625                 630                 635                 640
Phe Ser Thr His Tyr Phe Gln Gln Lys Val Phe Val Leu Leu Ala Ala
                645                 650                 655
Leu Arg Pro Gln Trp Cys Ser Arg Glu Ile Pro Asp Pro Ala Asn Ser
                660                 665                 670
Thr Cys Ala Lys Lys Tyr Pro Ile Ala Glu Glu Lys Thr Gln Leu Pro
                675                 680                 685
Leu Asp Arg Leu Leu Ile Asp Trp Pro Thr Pro Glu Asp Pro Glu Pro
                690                 695                 700
```

```
Leu Val Ile Ser Glu Val Leu His Gln Val Thr Pro Val Phe Arg His
705                 710                 715                 720

Pro Pro Cys Ser Asn Trp Pro Gln Arg Glu Lys Gly Ile Gln Gly His
            725                 730                 735

Gln Ala Ser Glu Lys Asp Met Met His Ser Ala Ser Ser Pro Pro
        740                 745                 750

Pro Arg Ala Leu Gln Ala Glu Ser Arg Gln Leu Val Asp Leu Tyr Lys
        755                 760                 765

Val Leu Glu Ser Arg Gly Ser Asp Pro Lys Pro Glu Asn Pro Ala Cys
770                 775                 780

Pro Trp Thr Val Leu Pro Ala Gly Asp Leu Pro Thr His Asp Gly Tyr
785                 790                 795                 800

Leu Pro Ser Asn Ile Asp Asp Leu Pro Ser His Glu Ala Pro Leu Ala
            805                 810                 815

Asp Ser Leu Glu Glu Leu Glu Pro Gln His Ile Ser Leu Ser Val Phe
            820                 825                 830

Pro Ser Ser Ser Leu His Pro Leu Thr Phe Ser Cys Gly Asp Lys Leu
            835                 840                 845

Thr Leu Asp Gln Leu Lys Met Arg Cys Asp Ser Leu Met Leu
    850                 855                 860

(2) INFORMATION FOR SEQ ID NO:3:

(i) SEQUENCE CHARACTERISTICS:
        (A) LENGTH: 2104 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (A) ORGANISM: Homo sapiens
        (G) CELL TYPE: human T-cells (vii) IMMEDIATE SOURCE:
        (A) LIBRARY: library 3 day PHA/pEF-BOS
        (B) CLONE: human interleukin-12 receptor clone #5

(ix) FEATURE:
        (A) NAME/KEY: CDS
        (B) LOCATION: 65..2050

(xi) SEQUENCE DESCRIPTION: SEQ ID NO:3:

GGTGGCTGAA CCTCGCAGGT GGCAGAGAGG CTCCCCTGGG GCTGTGGGGC TCTACGTGGA    60

TCCG ATG GAG CCG CTG GTG ACC TGG GTG GTC CCC CTC CTC TTC CTC TTC   109
     Met Glu Pro Leu Val Thr Trp Val Val Pro Leu Leu Phe Leu Phe
     1               5                   10                  15

CTG CTG TCC AGG CAG GGC GCT GCC TGC AGA ACC AGT GAG TGC TGT TTT   157
Leu Leu Ser Arg Gln Gly Ala Ala Cys Arg Thr Ser Glu Cys Cys Phe
                20                  25                  30

CAG GAC CCG CCA TAT CCG GAT GCA GAC TCA GGC TCG GCC TCG GGC CCT   205
Gln Asp Pro Pro Tyr Pro Asp Ala Asp Ser Gly Ser Ala Ser Gly Pro
            35                  40                  45

AGG GAC CTG AGA TGC TAT CGG ATA TCC AGT GAT CGT TAC GAG TGC TCC   253
Arg Asp Leu Arg Cys Tyr Arg Ile Ser Ser Asp Arg Tyr Glu Cys Ser
        50                  55                  60

TGG CAG TAT GAG GGT CCC ACA GCT GGG GTC AGC CAC TTC CTG CGG TGT   301
Trp Gln Tyr Glu Gly Pro Thr Ala Gly Val Ser His Phe Leu Arg Cys
    65                  70                  75

TGC CTT AGC TCC GGG CGC TGC TGC TAC TTC GCC GCC GGC TCA GCC ACC   349
```

```
Cys Leu Ser Ser Gly Arg Cys Cys Tyr Phe Ala Ala Gly Ser Ala Thr
 80                  85                  90                  95

AGG CTG CAG TTC TCC GAC CAG GCT GGG GTG TCT GTG CTG TAC ACT GTC       397
Arg Leu Gln Phe Ser Asp Gln Ala Gly Val Ser Val Leu Tyr Thr Val
                    100                 105                 110

ACA CTC TGG GTG GAA TCC TGG GCC AGG AAC CAG ACA GAG AAG TCT CCT       445
Thr Leu Trp Val Glu Ser Trp Ala Arg Asn Gln Thr Glu Lys Ser Pro
                115                 120                 125

GAG GTG ACC CTG CAG CTC TAC AAC TCA GTT AAA TAT GAG CCT CCT CTG       493
Glu Val Thr Leu Gln Leu Tyr Asn Ser Val Lys Tyr Glu Pro Pro Leu
            130                 135                 140

GGA GAC ATC AAG GTG TCC AAG TTG GCC GGG CAG CTG CGT ATG GAG TGG       541
Gly Asp Ile Lys Val Ser Lys Leu Ala Gly Gln Leu Arg Met Glu Trp
        145                 150                 155

GAG ACC CCG GAT AAC CAG GTT GGT GCT GAG GTG CAG TTC CGG CAC CGG       589
Glu Thr Pro Asp Asn Gln Val Gly Ala Glu Val Gln Phe Arg His Arg
160                 165                 170                 175

ACA CCC AGC AGC CCA TGG AAG TTG GGC GAC TGC GGA CCT CAG GAT GAT       637
Thr Pro Ser Ser Pro Trp Lys Leu Gly Asp Cys Gly Pro Gln Asp Asp
                    180                 185                 190

GAT ACT GAG TCC TGC CTC TGC CCC CTG GAG ATG AAT GTG GCC CAG GAA       685
Asp Thr Glu Ser Cys Leu Cys Pro Leu Glu Met Asn Val Ala Gln Glu
                195                 200                 205

TTC CAG CTC CGA CGA CGG CAG CTG GGG AGC CAA GGA AGT TCC TGG AGC       733
Phe Gln Leu Arg Arg Arg Gln Leu Gly Ser Gln Gly Ser Ser Trp Ser
            210                 215                 220

AAG TGG AGC AGC CCC GTG TGC GTT CCC CCT GAA AAC CCC CCA CAG CCT       781
Lys Trp Ser Ser Pro Val Cys Val Pro Pro Glu Asn Pro Pro Gln Pro
        225                 230                 235

CAG GTG AGA TTC TCG GTG GAG CAG CTG GGC CAG GAT GGG AGG AGG CGG       829
Gln Val Arg Phe Ser Val Glu Gln Leu Gly Gln Asp Gly Arg Arg Arg
240                 245                 250                 255

CTG ACC CTG AAA GAG CAG CCA ACC CAG CTG GAG CTT CCA GAA GGC TGT       877
Leu Thr Leu Lys Glu Gln Pro Thr Gln Leu Glu Leu Pro Glu Gly Cys
                    260                 265                 270

CAA GGG CTG GCG CCT GGC ACG GAG GTC ACT TAC CGA CTA CAG CTC CAC       925
Gln Gly Leu Ala Pro Gly Thr Glu Val Thr Tyr Arg Leu Gln Leu His
                275                 280                 285

ATG CTG TCC TGC CCG TGT AAG GCC AAG GCC ACC AGG ACC CTG CAC CTG       973
Met Leu Ser Cys Pro Cys Lys Ala Lys Ala Thr Arg Thr Leu His Leu
            290                 295                 300

GGG AAG ATG CCC TAT CTC TCG GGT GCT GCC TAC AAC GTG GCT GTC ATC      1021
Gly Lys Met Pro Tyr Leu Ser Gly Ala Ala Tyr Asn Val Ala Val Ile
        305                 310                 315

TCC TCG AAC CAA TTT GGT CCT GGC CTG AAC CAG ACG TGG CAC ATT CCT      1069
Ser Ser Asn Gln Phe Gly Pro Gly Leu Asn Gln Thr Trp His Ile Pro
320                 325                 330                 335

GCC GAC ACC CAC ACA GAA CCA GTG GCT CTG AAT ATC AGC GTC GGA ACC      1117
Ala Asp Thr His Thr Glu Pro Val Ala Leu Asn Ile Ser Val Gly Thr
                    340                 345                 350

AAC GGG ACC ACC ATG TAT TGG CCA GCC CGG GCT CAG AGC ATG ACG TAT      1165
Asn Gly Thr Thr Met Tyr Trp Pro Ala Arg Ala Gln Ser Met Thr Tyr
                355                 360                 365

TGC ATT GAA TGG CAG CCT GTG GGC CAG GAC GGG GGC CTT GCC ACC TGC      1213
Cys Ile Glu Trp Gln Pro Val Gly Gln Asp Gly Gly Leu Ala Thr Cys
            370                 375                 380

AGC CTG ACT GCG CCG CAA GAC CCG GAT CCG GCT GGA ATG GCA ACC TAC      1261
Ser Leu Thr Ala Pro Gln Asp Pro Asp Pro Ala Gly Met Ala Thr Tyr
        385                 390                 395

AGC TGG AGT CGA GAG TCT GGG GCA ATG GGG CAG GAA AAG TGT TAC TAC      1309
```

```
Ser Trp Ser Arg Glu Ser Gly Ala Met Gly Gln Glu Lys Cys Tyr Tyr
400                 405                 410                 415

ATT ACC ATC TTT GCC TCT GCG CAC CCC GAG AAG CTC ACC TTG TGG TCT         1357
Ile Thr Ile Phe Ala Ser Ala His Pro Glu Lys Leu Thr Leu Trp Ser
                420                 425                 430

ACG GTC CTG TCC ACC TAC CAC TTT GGG GGC AAT GCC TCA GCA GCT GGG         1405
Thr Val Leu Ser Thr Tyr His Phe Gly Gly Asn Ala Ser Ala Ala Gly
            435                 440                 445

ACA CCG CAC CAC GTC TCG GTG AAG AAT CAT AGC TTG GAC TCT GTG TCT         1453
Thr Pro His His Val Ser Val Lys Asn His Ser Leu Asp Ser Val Ser
        450                 455                 460

GTG GAC TGG GCA CCA TCC CTG CTG AGC ACC TGT CCC GGC GTC CTA AAG         1501
Val Asp Trp Ala Pro Ser Leu Leu Ser Thr Cys Pro Gly Val Leu Lys
    465                 470                 475

GAG TAT GTT GTC CGC TGC CGA GAT GAA GAC AGC AAA CAG GTG TCA GAG         1549
Glu Tyr Val Val Arg Cys Arg Asp Glu Asp Ser Lys Gln Val Ser Glu
480                 485                 490                 495

CAT CCC GTG CAG CCC ACA GAG ACC CAA GTT ACC CTC AGT GGC CTG CGG         1597
His Pro Val Gln Pro Thr Glu Thr Gln Val Thr Leu Ser Gly Leu Arg
                500                 505                 510

GCT GGT GTA GCC TAC ACG GTG CAG GTG CGA GCA GAC ACA GCG TGG CTG         1645
Ala Gly Val Ala Tyr Thr Val Gln Val Arg Ala Asp Thr Ala Trp Leu
                515                 520                 525

AGG GGT GTC TGG AGC CAG CCC CAG CGC TTC AGC ATC GAA GTG CAG GTT         1693
Arg Gly Val Trp Ser Gln Pro Gln Arg Phe Ser Ile Glu Val Gln Val
            530                 535                 540

TCT GAT TGG CTC ATC TTC TTC GCC TCC CTG GGG AGC TTC CTG AGC ATC         1741
Ser Asp Trp Leu Ile Phe Phe Ala Ser Leu Gly Ser Phe Leu Ser Ile
        545                 550                 555

CTT CTC GTG GGC GTC CTT GGC TAC CTT GGC CTG AAC AGG GCC GCA CGG         1789
Leu Leu Val Gly Val Leu Gly Tyr Leu Gly Leu Asn Arg Ala Ala Arg
560                 565                 570                 575

CAC CTG TGC CCG CCG CTG CCC ACA CCC TGT GCC AGC TCC GCC ATT GAG         1837
His Leu Cys Pro Pro Leu Pro Thr Pro Cys Ala Ser Ser Ala Ile Glu
                580                 585                 590

TTC CCT GGA GGG AAG GAG ACT TGG CAG TGG ATC AAC CCA GTG GAC TTC         1885
Phe Pro Gly Gly Lys Glu Thr Trp Gln Trp Ile Asn Pro Val Asp Phe
                595                 600                 605

CAG GAA GAG GCA TCC CTG CAG GAG GCC CTG GTG GTA GAG ATG TCC TGG         1933
Gln Glu Glu Ala Ser Leu Gln Glu Ala Leu Val Val Glu Met Ser Trp
            610                 615                 620

GAC AAA GGC GAG AGG ACT GAG CCT CTC GAG AAG ACA GAG CTA CCT GAG         1981
Asp Lys Gly Glu Arg Thr Glu Pro Leu Glu Lys Thr Glu Leu Pro Glu
        625                 630                 635

GGT GCC CCT GAG CTG GCC CTG GAT ACA GAG TTG TCC TTG GAG GAT GGA         2029
Gly Ala Pro Glu Leu Ala Leu Asp Thr Glu Leu Ser Leu Glu Asp Gly
640                 645                 650                 655

GAC AGG TGC AAG GCC AAG ATG TGATCGTTGA GGCTCAGAGA GGGTGAGTGA            2080
Asp Arg Cys Lys Ala Lys Met
                660

CTCGCCCGAG GCTACGTAGC CTTT                                              2104

(2) INFORMATION FOR SEQ ID NO:4:

(i) SEQUENCE CHARACTERISTICS:
        (A) LENGTH: 662 amino acids
        (B) TYPE: amino acid
        (D) TOPOLOGY: linear (ii) MOLECULE TYPE: protein (ix) FEATURE:
```

(A) NAME/KEY: Region
          (B) LOCATION: 1..20
          (D) OTHER INFORMATION: /note= "N-terminal signal peptide
              (1..20 or 23 or 24)"

(ix) FEATURE:
          (A) NAME/KEY: Region
          (B) LOCATION: 541..570
          (D) OTHER INFORMATION: /note= "transmembrane region"

(ix) FEATURE:
          (A) NAME/KEY: Region
          (B) LOCATION: 571..662
          (D) OTHER INFORMATION: /note= "cytoplasmic tail region"

(ix) FEATURE:
          (A) NAME/KEY: Region
          (B) LOCATION: 52..64
          (D) OTHER INFORMATION: /note= "sequence motif of cytokine
              receptor superfamily Cys52..Cys62SW"

(ix) FEATURE:
          (A) NAME/KEY: Region
          (B) LOCATION: 222..226
          (D) OTHER INFORMATION: /note= "cytokine receptor
              superfamily motif (W222SKWS)"

(ix) FEATURE:
          (A) NAME/KEY: Region
          (B) LOCATION: 121..123
          (D) OTHER INFORMATION: /note= "N-linked glycosylation
              site"

(ix) FEATURE:
          (A) NAME/KEY: Region
          (B) LOCATION: 329..331
          (D) OTHER INFORMATION: /note= "N-linked glycosylation
              site"

(ix) FEATURE:
          (A) NAME/KEY: Region
          (B) LOCATION: 346..348
          (D) OTHER INFORMATION: /note= "N-linked glycosylation
              site"

(ix) FEATURE:
          (A) NAME/KEY: Region
          (B) LOCATION: 352..354
          (D) OTHER INFORMATION: /note= "N-linked glycosylation
              site"

(ix) FEATURE:
          (A) NAME/KEY: Region
          (B) LOCATION: 442..444
          (D) OTHER INFORMATION: /note= "N-linked glycosylation
              site"

(ix) FEATURE:
          (A) NAME/KEY: Region
          (B) LOCATION: 456..458
          (D) OTHER INFORMATION: /note= "N-linked glycosylation
              site"

(ix) FEATURE:
          (A) NAME/KEY: Region
          (B) LOCATION: 24..540
          (D) OTHER INFORMATION: /note= "Extracellular region"

(xi) SEQUENCE DESCRIPTION: SEQ ID NO:4:

Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
                20                  25                  30

Asp Pro Pro Tyr Pro Asp Ala Asp Ser Gly Ser Ala Ser Gly Pro Arg
            35                  40                  45

Asp Leu Arg Cys Tyr Arg Ile Ser Ser Asp Arg Tyr Glu Cys Ser Trp

-continued

```
                50                  55                  60
Gln Tyr Glu Gly Pro Thr Ala Gly Val Ser His Phe Leu Arg Cys Cys
 65                  70                  75                  80
Leu Ser Ser Gly Arg Cys Cys Tyr Phe Ala Ala Gly Ser Ala Thr Arg
                 85                  90                  95
Leu Gln Phe Ser Asp Gln Ala Gly Val Ser Val Leu Tyr Thr Val Thr
                100                 105                 110
Leu Trp Val Glu Ser Trp Ala Arg Asn Gln Thr Glu Lys Ser Pro Glu
                115                 120                 125
Val Thr Leu Gln Leu Tyr Asn Ser Val Lys Tyr Glu Pro Pro Leu Gly
130                 135                 140
Asp Ile Lys Val Ser Lys Leu Ala Gly Gln Leu Arg Met Glu Trp Glu
145                 150                 155                 160
Thr Pro Asp Asn Gln Val Gly Ala Glu Val Gln Phe Arg His Arg Thr
                165                 170                 175
Pro Ser Ser Pro Trp Lys Leu Gly Asp Cys Gly Pro Gln Asp Asp Asp
                180                 185                 190
Thr Glu Ser Cys Leu Cys Pro Leu Glu Met Asn Val Ala Gln Glu Phe
                195                 200                 205
Gln Leu Arg Arg Arg Gln Leu Gly Ser Gln Gly Ser Ser Trp Ser Lys
                210                 215                 220
Trp Ser Ser Pro Val Cys Val Pro Glu Asn Pro Pro Gln Pro Gln
225                 230                 235                 240
Val Arg Phe Ser Val Glu Gln Leu Gly Gln Asp Gly Arg Arg Arg Leu
                245                 250                 255
Thr Leu Lys Glu Gln Pro Thr Gln Leu Glu Leu Pro Glu Gly Cys Gln
                260                 265                 270
Gly Leu Ala Pro Gly Thr Glu Val Thr Tyr Arg Leu Gln Leu His Met
                275                 280                 285
Leu Ser Cys Pro Cys Lys Ala Lys Ala Thr Arg Thr Leu His Leu Gly
                290                 295                 300
Lys Met Pro Tyr Leu Ser Gly Ala Ala Tyr Asn Val Ala Val Ile Ser
305                 310                 315                 320
Ser Asn Gln Phe Gly Pro Gly Leu Asn Gln Thr Trp His Ile Pro Ala
                325                 330                 335
Asp Thr His Thr Glu Pro Val Ala Leu Asn Ile Ser Val Gly Thr Asn
                340                 345                 350
Gly Thr Thr Met Tyr Trp Pro Ala Arg Ala Gln Ser Met Thr Tyr Cys
                355                 360                 365
Ile Glu Trp Gln Pro Val Gly Gln Asp Gly Gly Leu Ala Thr Cys Ser
                370                 375                 380
Leu Thr Ala Pro Gln Asp Pro Asp Pro Ala Gly Met Ala Thr Tyr Ser
385                 390                 395                 400
Trp Ser Arg Glu Ser Gly Ala Met Gly Gln Glu Lys Cys Tyr Tyr Ile
                405                 410                 415
Thr Ile Phe Ala Ser Ala His Pro Glu Lys Leu Thr Leu Trp Ser Thr
                420                 425                 430
Val Leu Ser Thr Tyr His Phe Gly Gly Asn Ala Ser Ala Ala Gly Thr
                435                 440                 445
Pro His His Val Ser Val Lys Asn His Ser Leu Asp Ser Val Ser Val
                450                 455                 460
Asp Trp Ala Pro Ser Leu Leu Ser Thr Cys Pro Gly Val Leu Lys Glu
465                 470                 475                 480
```

-continued

```
Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
        515                 520                 525

Gly Val Trp Ser Gln Pro Gln Arg Phe Ser Ile Glu Val Gln Val Ser
    530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
        595                 600                 605

Glu Glu Ala Ser Leu Gln Glu Ala Leu Val Val Glu Met Ser Trp Asp
    610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                645                 650                 655

Arg Cys Lys Ala Lys Met
            660
```